United States Patent [19]

Usagawa et al.

[11] 4,071,365
[45] Jan. 31, 1978

[54] SILVER HALIDE EMULSION CONTAINING TWO-EQUIVALENT YELLOW DYE-FORMING COUPLER

[75] Inventors: Yasushi Usagawa; Kiyoshi Yamashita; Mamoru Nakatani; Kosaku Masuda; Satoshi Kawakatsu, all of Nagaokakyo, Japan

[73] Assignee: Mitsubishi Paper Mills, Ltd., Tokyo, Japan

[21] Appl. No.: 723,163

[22] Filed: Sept. 14, 1976

[30] Foreign Application Priority Data

Sept. 16, 1975  Japan ............................... 50-111872

[51] Int. Cl.² .......................... G03C 7/00; G03C 1/40
[52] U.S. Cl. .................................... 96/56.5; 96/100 N
[58] Field of Search .................... 96/100, 56.5, 100 N

[56] References Cited

U.S. PATENT DOCUMENTS

| 3,632,373 | 1/1972 | O'Connell et al. | 96/100 |
|---|---|---|---|
| 3,703,375 | 11/1972 | Groet et al. | 96/100 |
| 3,961,963 | 6/1976 | Shiba et al. | 96/100 |

*Primary Examiner*—J. Travis Brown
*Attorney, Agent, or Firm*—Cushman, Darby & Cushman

[57] ABSTRACT

A compound represented by the general formula A-Q (wherein A represents a yellow dye image-forming coupler residue having the active methylene group from which one hydrogen atom has been replaced and Q represents a tetrazolyl group substituted at the 5-position with hydrogen, a halogen, a cyano, an alkyl, an aralkyl, an aryl, an alkyl-amino or an arylamino group) is used as a yellow dye image-forming coupler for obtaining yellow dye images that have good spectral absorption characteristics, and good stability to prolonged exposure to light, heat and high humidity.

10 Claims, No Drawings

SILVER HALIDE EMULSION CONTAINING TWO-EQUIVALENT YELLOW DYE-FORMING COUPLER

BACKGROUND OF THE INVENTION

1. Field of the Invention

The present invention relates to photography and particularly to new yellow dye image-forming couplers and to a method for forming yellow dye images by using the same.

2. Description of the Prior Art

The color developing method in color photography, namely, the formation of colored photographic images by the coupling of oxidized developers (oxidized aromatic primary amino developing agents) with couplers is well known. Among the yellow dye image-forming couplers used in said photographic process the so-called four-equivalent couplers have active methylene group which can couple with the oxidized aromatic primary amino developing agents to form yellow dye. Said four-equivalent couplers require reduction of four molecules of silver halide in order to form one molecule of dye by coupling with color developer. However, it is known that couplers in which one of hydrogen atoms in active methylene group is substituted with a substituent such as a halogen atom can also form the same dye as formed from unsubstituted couplers. In this case, said substituent (a splitting off group) is easily released on coupling and reduction of only two molecules of silver halide is required for formation of one molecule of dye. Therefore, these couplers are called two-equivalent couplers. Use of the two-equivalent couplers improves coupling reactivity over use of the four-equivalent couplers. Therefore, when the two-equivalent couplers are employed, obviating prolonged development makes it possible to provide color photographic light-sensitive materials suitable for rapid color developing process. Moreover, color photographic light-sensitive materials which contain two-equivalent coupler in silver halide emulsion require the silver halide in the amount of one-half that of silver halide required by the four-equivalent coupler and hence cost can be reduced. Furthermore, the emulsion layer can be made thinner to increase resolving power and sharpness of color image. Thus, the two-equivalent couplers are more desirable for color photography than the four-equivalent couplers. However, certain of the two-equivalent couplers do not have so high coupling reactivity or tend to produce color stains such as fog.

SUMMARY OF THE INVENTION

It is therefore an object of the present invention to provide novel two-equivalent yellow couplers which overcome said defects.

Another object of the present invention is to provide a method for formation of yellow images of color photographic light-sensitive material by using said novel two-equivalent yellow couplers.

These objects of the present invention are accomplished by the preparation and use of the two-equivalent couplers of the present invention. The yellow dye image-forming couplers of the present invention are represented by the general formula A-Q [wherein A represents a yellow dye image-forming coupler residue having active methylene group from which one hydrogen atom has been replaced and Q represents tetrazolyl group substituted with hydrogen, halogen, cyano, alkyl (e.g., substituted or unsubstituted lower alkyl), aralkyl (e.g., benzyl, phenethyl, etc.), aryl (e.g., substituted or unsubstituted phenyl), alkylamino (e.g., lower alkylamino) or arylamino (e.g., substituted or unsubstituted anilino) at the 5-position]. These couplers of the present invention are incorporated into silver halide emulsion layer or color developer solution.

Among the couplers mentioned above, those which have the following formula are especially preferred.

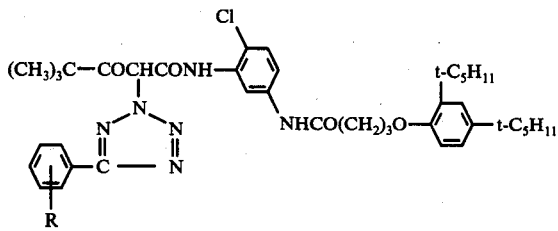

(wherein R is hydrogen, a halogen, a lower alkyl or a lower alkoxy).

The compounds represented by the said general formula can generally be synthesized by reacting A-X (wherein A represents a yellow-dye image-forming coupler residue having active methylene group from which one hydrogen atoms has been replaced and X represents a halogen atom) with

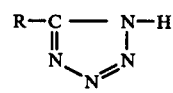

(wherein R represents hydrogen, halogen, cyano, alkyl (e.g., substituted or unsubstituted lower alkyl), aralkyl (e.g., benzyl, phenethyl, etc.), aryl (e.g., substituted or unsubstituted phenyl), alkylamino (e.g., lower alkylamino) or arylamino (e.g., substituted or unsubstituted anilino). In this case, said tetrazolyl group attaches to carbon atom in the active methine group of the coupler residue at 1-or 2-position.

The two-equivalent yellow couplers having tetrazolyl group as a splitting off group as of the present invention, in spite of their high coupling reactivity, cause little color stains such as fog which are caused by other conventional two-equivalent couplers. This is an interesting phenomenon in view of the fact that tetrazole released from couplers at color development is widely used as an anti-fogging agent in photographic emulsions. Moreover, the dyes formed from the two-equivalent yellow couplers of the present invention by color development exhibit excellent light, heat and humidity fastness and have excellent spectral absorption characteristics.

Included among the present novel two-equivalent couplers are the following typical examples which are used to illustrate but not limit the present invention.

1. α-pivaloyl-α-(5-phenyl-2-tetrazolyl)-2-chloro-5-[γ-(2,4-di-tert-pentylphenoxy)-butyramido]acetanilide
2. α-pivaloyl-α-(5-phenyl-2-tetrazolyl)-acetanilide
3. α-benzoyl-α-(5-ethylaminotetrazolyl)-acetanilide
4. α-pivaloyl-α-[5-(2-chlorophenyl)-2-tetrazolyl]-2-chloro-5-[γ-(2,4-di-tert-pentyl phenoxy)-butyramido]acetanilide 5. α-pivaloyl-α-tetrazolyl-2-chloro-acetanilide
6. α-(2-methoxybenzoyl)-α-(5-methyltetrazolyl)-acetanilide
7. α-benzoyl-α-(5-benzyltetrazolyl)-2-chloro-5-[γ-(2,4-di-tert-pentylphenoxy)butyramido]-acetanilide
8. α-(2-fluorobenzoyl)-α-(5-trifluoromethyl tetrazolyl)-2-dodecyloxyacetanilide
9. α-(2-methoxybenzoyl)-α-(5-anilinotetrazolyl)-2-chloro-5-[γ-(2,4-di-tert-pentylphenoxy)-butyramido]acetanilide
10. α-pivaloyl-α-(5-cyanotetrazolyl)-2-methoxy-4-[α-(2,4-di-tert-pentylphenoxy)acetamido]acetanilide
11. α-pivaloyl-α-[5-(4-chlorophenyl)-2-tetrazolyl]-2-chloro-5-[γ-(2,4-di-tert-pentyl phenoxy)-butyramido]acetanilide
12. α-pivaloyl-α-[5-(2-methylphenyl)-2-tetrazolyl]-2-chloro-5-[α-(2,4-di-tert-pentylphenoxy)-butyramido]acetanilide
13. α-pivaloyl-α-[5-(2-methoxyphenyl)-2-tetrazolyl]-2-chloro-5-[α-(2,4-di-tert-pentylphenoxy)-butyramido]acetanilide
14. α-pivaloyl-α-[5-(4-methoxyphenyl)-2-tetrazolyl]-2-chloro-5-[α-(2,4-di-tert-pentylphenoxy)-butyramido]acetanilide Said compounds can generally be synthesized by the reaction of couplers in which one of hydrogen atoms of active methylene group of yellow couplers having active methylene group is substituted with a halogen atom with tetrazoles substituted at 5-position.

The preparation of the present couplers is illustrated by a description of representative couplers of the present invention.

Coupler (1)

A mixture of 4.8 g of α-pivaloyl-α-chloro-2-chloro-5-[γ-(2,4-di-tert-pentylphenoxy)butyramido]-acetanilide, 1.3 g of 5-phenyltetrazole and 1.0 g of triethylamine in 40 ml of acetonitrile was refluxed for 3 hours. Thereafter, the reaction mixture was concentrated and the resultant residue was recrystallized from cyclohexane to obtain 3.2 g of white powders having a melting point of 81°–83° C.

| Elementary analytical values (%) | C | H | N |
|---|---|---|---|
| Calcd. | 67.16 | 7.19 | 11.75 |
| Found | 67.10 | 7.20 | 11.87 |

Coupler (2)

A mixture of 4.0 g of α-pivaloyl-α-chloroacetanilide, 2.6 g of 5-phenyltetrazole and 1.9 of triethylamine in 40 ml of acetonitrile was refluxed for 2 hours. Then the reaction mixture was concentrated and resultant residue was recrystallized from cyclohexane, yielding 3.6 g of white powders having a melting point of 144°–146° C.

| Elementary analytical values (%) | C | H | N |
|---|---|---|---|
| Calcd. | 66.10 | 5.82 | 19.27 |
| Found | 66.07 | 5.83 | 18.91 |

The couplers of the present invention may be incorporated into color photographic light sensitive materials by the known methods. That is, they may be contained in color developer solutions as diffusible couplers or they may be dissolved in high boiling solvents such as dibutyl phthalate, diethyl succinate, tricresyl phosphate, etc. and auxiliary solvents such as ethyl acetate, etc., then dispersed in hydrophilic high polymer containing surfactants, e.g., an aqueous gelatin solution and the dispersion may be added to silver halide emulsion as nondiffusing couplers. This emulsion can be coated on a wide variety of photographic emulsion supports such as film bases, baryta paper, laminated papers and any other known supports. Furthermore, said silver halide emulsion may contain the known various sensitizers, stabilizers, hardeners, antioxidants, scavengers and other additives usually added to silver halide color photographic light sensitive materials. Thus obtained color photographic light sensitive materials may be developed with developers which are used for development of ordinary color photographic light sensitive materials and which contain P-aminophenol, N,N-di-substituted-P-phenylenediamine, etc. as color developing agent.

The coupler may be added in the range of 0.01 – 3 (molar ratio to silver halide), preferably 0.1 – 2.

The following examples show that the couplers of the present invention have a high color forming efficiency without any adverse effects on photographic characteristics and the yellow dye images obtained by color development exhibit excellent light, heat and humidity fastness and have excellent spectral absorption characteristics.

EXAMPLE 1

$4 \times 10^{-3}$ mol of a coupler shown in Table 1 was dissolved in a mixed solvent of 4 ml of dibutyl phthalate and 10 ml of ethyl acetate at 60° C. The resultant solution was added to 70 ml of aqueous solution containing 3.5 g of gelatin and 0.25 g of sodium dodecylbenzenesulfonate at 40° C and this was vigorously agitated and dispersed by a homogenizer to obtain dispersions of the couplers. Each of these dispersions was mixed with 400 g of photographic emulsion containing 20 g of gelatin and $8 \times 10^{-2}$ mols of silver chlorobromide (silver bromide 75 mol % and silver chloride 25 mol %). To the mixture was added 10 ml of 3% methanolic solution of 1,3,5-triacryloyl-hexahydro-S-triazine as a hardener. After the final pH was adjusted to 6.2, this was coated on a polyester film base and was dried. The resultant light sensitive material was exposed and then developed with a developer of the following compositions at 25° C for 6 minutes.

| | | |
|---|---|---|
| Sodium hydroxide | 1.65 | g |
| Sodium metaborate | 50 | g |
| Anhydrous sodium sulfite | 1.8 | g |
| Potassium bromide | 0.5 | g |
| 4-Amino-N-ethyl-N-(β-methane-sulfonamidoethyl)-m-toluidinesesquisulfate monohydrate | 4.4 | g |
| Sodium hexametaphosphate | 0.5 | g |
| Hydroxylamine hydrochloride | 1.0 | g |
| Benzyl alcohol | 24 | ml |
| Diethylene glycol | 10 | ml |
| Water to | 1 | l |

Then, the developed material was bleached and fixed in ethylenediaminetetraacetate (EDTA)-iron salt bleaching and fixing solution having the following composition at 25° C for 4 minutes.

| | | |
|---|---|---|
| EDTA-iron salt | 56 | g |
| EDTA-disodium salt | 2 | g |
| Ammonium thiosulfate | 60 | g |

|  |  |
|---|---|
| Anhydrous sodium sulfite | 20 g |
| Disodium phosphate | 12 g |
| Sodium hydrogensulfite | 5 g |
| Water to | 1 l |

Thereafter, the material was washed with water for 8 minutes, then dipped in a stabilizing bath at 25° C for 3 minutes and dried. Spectral absorption distribution of yellow images thus obtained was measured by a spectrophotometer (UV-200 manufactured by Shimazu Seisakusho K.K.) to obtain the results as shown in Table 1.

As comparative couplers, the following known four-equivalent couplers corresponding to the present two equivalent couplers were used. That is, α-pivaloyl-2-chloro-5-[γ-(2,4-di-tert-pentylphenoxy)butyramido]-acetanilide (Coupler I), α-benzoyl-2-chloro-5-[γ-(2,4-di-tert-pentylphenoxy)butyramido]acetanilide (Coupler II) and α-(2-methoxybenzoyl)-2-chloro-5-[γ-(2,4-di-tert-pentylphenoxy)butyramido]acetanilide (Coupler III).

Table 1

| Couplers | (1) | (I)* | (7) | (II)* | (9) | (III)* |
|---|---|---|---|---|---|---|
| Absorption maximum wavelength (nm) | 440 | 439 | 447 | 446 | 434 | 434 |

*The comparative couplers which are not included in the present invention.

As is clear from Table 1, the yellow dye images produced from the present couplers (1), (7) and (9) have nearly the same absorption maximum wavelength and spectral absorption distribution as the yellow dye images produced from the comparative four equivalent couplers (I), (II) and (III). This fact shows that introduction of tetrazole groups as splitting off group into four-equivalent couplers results in no adverse effects on spectral absorption distribution as seen in the known two equivalent couplers.

EXAMPLE 2

Light sensitive materials produced in the same manner as in Example 1 were developed with the same developer as used in Example 1 for 12 minutes without exposure and thereafter they were subjected to bleaching and fixing, washing with water and stabilizing treatment. Fog density of thus treated light sensitive materials was measured. The results are shown in Table 2. As comparative couplers, the couplers (I), (II) and (III) used in Example 1 and the known two-equivalent couplers, α-pivaloyl-α-chloro-2-chloro-5-[γ-(2,4-di-tert-pentylphenoxy)butyramido]acetanilide (coupler IV), α-benzoyl-α-chloro-2-chloro-5-[γ-(2,4-di-tert-pentylphenoxy)butyramido]acetanilide (coupler V) and α-(2-methoxybenzoyl)-α-chloro-2-chloro-5-[γ-(2,4-di-tert-pentylphenoxy)butyramido]acetanilide (coupler VI) were used. The density was measured by transmission densitometer TD-504 (manufactured by Macbeth Co., Ltd.) using Wratten filter No. 94 of Eastman Kodak Co.).

Table 2

|  | Couplers of the present invention | The known four-equivalent couplers | The known two-equivalent couplers |
|---|---|---|---|
| Compound | (4) | (I) | (IV) |
| Fog | 0.06 | 0.06 | 0.09 |
| Compound | (7) | (II) | (V) |
| Fog | 0.07 | 0.05 | 0.40 |

Table 2-continued

|  | Couplers of the present invention | The known four-equivalent couplers | The known two-equivalent couplers |
|---|---|---|---|
| Compound | (9) | (III) | (VI) |
| Fog | 0.07 | 0.06 | 0.20 |

Table 2 shows that the couplers of the present invention do not increase fogs as the known two-equivalent couplers do and cause only such fogs as the known four-equivalent couplers do. This fact shows that the tetrazoles are excellent splitting off groups which have overcome the defects of splitting off groups in the known two-equivalent couplers which increase the fogs.

EXAMPLE 3

Light sensitive materials produced in the same manner as in Example 1 were color developed, and subjected to bleaching and fixing, washing with water and stabilizing treatment in the same manner as in Example 1 without exposure. Color stains of these light sensitive materials caused when they were exposed to sun light for 4 weeks and when they were stored under a relative humidity of 80% for one month were measured. The results are shown in Table 3. The numerical values in this Table were obtained by measuring color stain density of the materials exposed to sun light and those stored as mentioned above in the same manner as in Example 2. Coupler (I) was used as the comparative coupler.

Table 3

| Couplers | (1) | (4) | (I)* |
|---|---|---|---|
| Increase in density due to exposure to sun light | 0.01 | 0.01 | 0.02 |
| Increase in density due to storage at 50° C and 80% RH | 0.01 | 0.01 | 0.01 |

*This coupler is not the coupler of the present invention.

Table 3 shows that the couplers of the present invention produce substantially no color stains due to light, heat and humidity like the comparative coupler (I). It is well known that the coupler (I) is stable to light, heat and humidity and causes substantially no color stain. This fact proves that introduction of tetrazoles as splitting off group does not reduce the stability of the couplers and the couplers of the present invention have no defects of the conventional two-equivalent couplers which produce color stains due to light, heat and humidity.

EXAMPLE 4

Light sensitive materials produced in the same manner as in Example 1 were exposed through an optical wedge and thereafter they were subjected to color development, bleaching and fixing, washing with water and stabilizing treatment in the same manner as in Example 1. The density of thus obtained samples was measured. Then, the samples were exposed to sun light for 4 weeks and reduction in the density of thus exposed samples was measured taking the density of the samples before exposre as 1.0. Furthermore, the samples obtained in the same manner as mentioned above were subjected to storage test of one month under the conditions of a temperature of 50° C and a relative humidity of 80%. Reduction in density of the samples after the test was measured taking the density before the test as 1.0. The results are shown in Table 4. As comparative couplers, said known couplers (I) and (IV) were used.

Table 4

|  | Coupler of the present invention | Known four-equivalent coupler | Known two-equivalent coupler |
| --- | --- | --- | --- |
| Coupler | (1) | (I) | (IV) |
| Reduction in density due to exposure to the sun light | 0.28 | 0.37 | 0.41 |
| Reduction in density under the conditions of 50° C and 80% RH | 0.05 | 0.10 | 0.07 |

Table 4 shows that the yellow dye images obtained from the couplers of the present invention are superior to those obtained from the known comparative couplers in light, heat and humidity fastness. This fact proves that the couplers of the present invention and the released tetrazoles do not adversely affect the fastness to light, heat and humidity of the images.

EXAMPLE 5

Light sensitive materials produced in the same manner as in Example 1 were exposed through an optical wedge and thereafter were subjected to color development, bleaching and fixing, washing with water and stabilizing treatment in the same manner as in Example 1 to obtain yellow dye images. Density of these yellow dye images was measured and the maximum density is shown in Table 5. The known four-equivalent coupler (I) used in Example 1, the known two-equivalent coupler (IV) used in Example 2 and the known two-equivalent coupler α-pivaloyl-α-succinimido-2-chloro-5-[γ-(2,4-di-tert-pentylphenoxy)butyramido]acetanilide (coupler VII) were used as comparative couplers.

Table 5

|  | The Present coupler | The comparative four-equivalent coupler | The comparative two-equivalent couplers | |
| --- | --- | --- | --- | --- |
| Compounds | (1) | (I) | (IV) | (VII) |
| Maximum density | 2.00 | 0.53 | 1.05 | 1.46 |

Table 5 shows that the dye image obtained using the present coupler had markedly higher maximum density than those obtained using the known four-equivalent and two-equivalent couplers. This fact proves the excellent color forming efficiency of the present couplers.

EXAMPLE 6

On a baryta paper were coated a halation preventing layer, a blue sensitive emulsion layer, an intermediate layer, a green sensitive emulsion layer, an ultraviolet absorbing layer, a red sensitive emulsion layer and finally an uppermost protective layer to obtain a color photographic paper. In the same manner as in Example 1, coupler (10) was added to the blue sensitive emulsion layer, 1-(2,4,6-trichlorophenyl)-3-(2-chloro-5-tetradecanoylaminoanilino)-2-pyrazoline-5-on (coupler VIII) was added to the green sensitive emulsion layer and 2-[α-(2,4-di-tert-pentylphenoxy)butyramido]-4,6-dichloro-5-methylphenol (coupler IX) was added to the red sensitive emulsion layer.

Thus obtained photographic paper was exposed to green and red through an optical wedge and was color developed in the same manner as in Example 1. Thus obtained magenta and cyan images were the same as those obtained from a photographic paper which was produced in the same manner as mentioned above without coating the blue sensitive emulsion layer and the intermediate layer and was exposed and color developed in the same manner as mentioned above. Furthermore, the yellow dye image obtained by exposing the former photographic paper (namely, which had the three emulsion layers) to blue through an optical wedge and color developing it in the same manner as in Example 1 had the harder tone, the higher maximum density and had less fog as compared with yellow dye image obtained from the same photographic paper exposed and color developed in the same manner as above except that the coupler (10) in the blue sensitive emulsion layer was replaced with coupler (IV).

What is claimed is:

1. A silver halide photographic emulsion comprising a silver halide and a binder which contains, as a yellow dye image-forming coupler, a compound represented by the general formula A–Q, wherein A represents a yellow dye image-forming coupler residue having the active methylene group from which one hydrogen atom has been replaced and Q represents a tetrazolyl group substituted at the 5-position with hydrogen, a halogen, a cyano, an alkyl, an aralkyl, an aryl, an alkyl-amino or an arylamino group, the tetrazolyl group being attached at the 1 or 2 position.

2. A color developer solution which contains, as a yellow dye image-forming coupler, a compound represented by the general formula A–Q, wherein A represents a yellow dye image-forming coupler residue having the active methylene group from which one hydrogen atom has been replaced and Q represents a tetrazolyl group substituted at the 5-position with hydrogen, a halogen, a cyano, an alkyl, an aralkyl, an aryl, an alkyl-amino or an arylamino group, the tetrazolyl group being attached at the 1 or 2 position, and a color developer.

3. An image-forming layer comprising a silver halide photographic emulsion according to claim 1.

4. A silver halide photographic emulsion according to claim 1, wherein the compound has the following general formula:

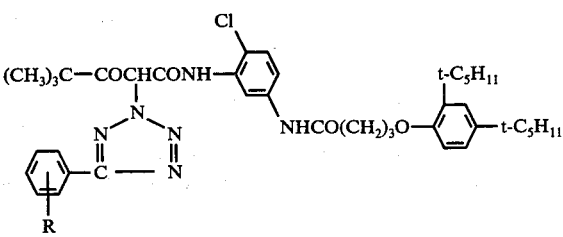

(wherein R is hydrogen, a halogen, a lower alkyl or lower alkoxy).

5. A color developer solution according to claim 2, wherein the compound has the following general formula:

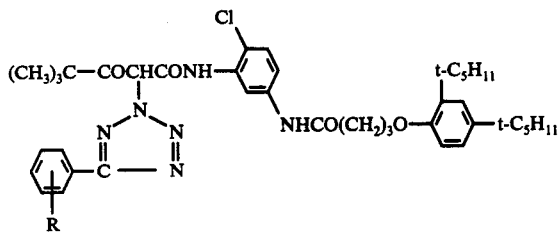

(wherein R is hydrogen, a halogen, a lower alkyl or lower alkoxy), and a color developer.

6. A silver halide photographic emulsion according to claim 1, wherein the compound is selected from the following group:
α-pivaloyl-α-(5-phenyl-2-tetrazolyl)-2-chloro-5-[γ-(2,4-di-tert-pentylphenoxy)-butyramido]acetanilide,
α-pivaloyl-α-[5-(2-chlorophenyl)-2-tetrazolyl]-2-chloro-5-[γ-(2,4-di-tert-pentylphenoxy)-butyramido]acetanilide,
α-pivaloyl-α-[5-(4-chlorophenyl)-2-tetrazolyl]-2-chloro-5-[γ-(2,4-di-tert-pentylphenoxy)-butyramido]acetanilide,
α-pivaloyl-α-[5-(2-methylphenyl)-2-tetrazolyl]-2-chloro-5-[γ-(2,4-di-tert-pentylphenoxy)-butyramido]acetanilide,
α-pivaloyl-α-[5-(2-methoxyphenyl)-2-tetrazolyl]-2-chloro-5-[γ-(2,4-di-tert-pentylphenoxy)-butyramido]acetanilide and α-pivaloyl-α-[5-(4-methoxyphenyl)-2-tetrazolyl]-2-chloro-5-[γ-(2,4-di-tert-pentylphenoxy)butyramido]acetanilide.

7. A silver halide photographic emulsion according to claim 1 wherein the tetrazolyl group is attached in the 2-position.

8. A silver halide photographic emulsion according to claim 1 wherein the compound is
1. α-pivaloyl-α-(5-phenyl-2-tetrazolyl)-2-chloro-5-[γ-(2,4-di-tert-pentylphenoxy)-butyramido]acetanilide;
2. α-pivaloyl-α-(4-phenyl-2-tetrazolyl)-acetanilide;
3. α-benzoyl-α-(5-ethylaminotetrazolyl)-acetanilide;
4. α-pivaloyl-α-[5-(2-chlorophenyl)-2-tetrazolyl]2-chloro-5-[γ:(2,4-di-tert-pentylphenoxy)-butyramido]acetanilide;
5. α-pivaloyl-α-tetrazolyl-2-chloro-acetanilide;
6. α-(2-methoxybenzoyl)-α-(5-methyletrazolyl)-acetanilide;
7. α-benzoyl-α-(5-benzyltetrazolyl)-2-chloro-5-[γ-(2,4-di-tert-pentylphenoxy)butyramido]-acetanilide;
8. α-(2-fluorobenzoyl)-α-(5-trifluoromethyltetrazolyl)-2-dodecyloxyacetanilide;
9. α-(2-methoxybenzoyl)-α-(5-anilinotetrazolyl)-2chloro-5-[γ-(2,4-di-tert-pentylphenoxy)-butyramido]acetanilide;
10. α-pivaloyl-α-(5-cyanotetrazolyl)-2-methoxy-4-[γ-(2,4-di-tert-pentylphenoxy)acetamido]-acetanilide;
11. α-pivaloyl-α-[5-(4-chlorophenyl)-2-tetrazolyl]-2-chloro-5-[γ-(2,4-di-tert-pentylphenoxy)-butyramido]acetanilide;
12. α-pivaloyl-α-[5-(2-methylphenyl)-2-tetrazolyl]-2-chloro-5-[γ-(2,4-di-tert-pentylphenoxy)-butyramido]acetanilide;
13. α-pivaloyl-α-[5-(2-methoxyphenyl)-2-tetrazolyl]-2-chloro-5-[γ-(2,4-di-tert-pentylphenoxy)-butyramido]acetanilide; or,
14. α-pivaloyl-α-[5-(4-methoxyphenyl)-2-tetrazolyl]-2-chloro-5-[γ-(2,4-di-tert-pentylphenoxy)-butyramido]acetanilide.

9. A color developer solution according to claim 2 wherein the tetrazolyl group is attached in the 2-position.

10. A color developer solution according to claim 2 wherein the compound is:
1. α-pivaloyl-α-(5-phenyl-2-tetrazolyl)-2-chloro-5-[γ-(2,4-tert-pentylphenoxy)-butyramido]acetanilide;
2. α-pivaloyl-α-(4-phenyl-2-tetrazolyl)-acetanilide;
3. α-benzoyl-α-(5-ethylaminotetrazolyl)-acetanilide;
4. α-pivaloyl-α-[5-(2-chlorophenyl)-2-tetrazolyl]-2-chloro-5-[γ-(2,4-di-tert-pentylphenoxy)-butyramido]acetanilide
5. α-pivaloyl-α-tetrazolyl-2-chloro-acetanilide;
6. α-(2-methoxybenzoyl)-α-(5-methyletrazolyl)-acetanilide;
7. α-benzoyl-α-(5-benzyltetrazolyl)-2-chloro-5-[γ-(2,4-di-tert-pentylphenoxy)butyramido]-acetanilide;
8. α-(2-fluorobenzoyl)-α-(5-trifluoromethyltetrazolyl)-2-dodecyloxyacetanilide;
9. α-(2-methoxybenzoyl)-α-(5-anilinotetrazolyl)-2-chloro-5-[γ(2,4-di-tert-pentylphenoxy)-butyramido]acetanilide;
10. α-pivaloyl-α-(5-cyanotetrazolyl)-2-methoxy-4-[γ-(2,4-di-tert-pentylphenoxy)acetamido]-acetanilide;
11. α-pivaloyl-α-[5-(4-chlorophenyl)-2-tetrazolyl]-2-chloro-5-[γ-(2,4-di-tert-pentylphenoxy)-butyramido]acetanilide;
12. α-pivaloyl-α-[5-(2-methylphenyl)-2-tetrazolyl]-2-chloro-5-[γ-(2,4-di-tert-pentylphenoxy)-butyramido]acetanilide;
13. α-pivaloyl-α-[5-(2-methoxyphenyl)-2-tetrazolyl]-2-chloro-5-[γ-(2,4-di-tert-pentylphenoxy)-butyramido]acetanilide; or,
14. α-pivaloyl-α-[5-(4-methoxyphenyl)-2-tetrazolyl]-2-chloro-5-[γ-(2,4-di-tert-pentylphenoxy)-butyramido]acetanilide.

* * * * *